United States Patent [19]
Maillard

[11] 3,935,255
[45] Jan. 27, 1976

[54] PHENYLACETIC ACID DERIVATIVES

[75] Inventor: Jacques Georges Maillard, Paris, France

[73] Assignee: Laboratoires Jacques Logeais, Issy-les-Moulineaux, France

[22] Filed: Aug. 28, 1974

[21] Appl. No.: 501,455

[30] Foreign Application Priority Data
Sept. 17, 1973 France ............................. 73.33276

[52] U.S. Cl. ............................. 260/518 R; 424/319
[51] Int. Cl.$^2$ .................. C07C 119/14; A01N 9/20
[58] Field of Search ........................ 260/519, 518 R

[56] References Cited
OTHER PUBLICATIONS
Theilheimer, W., Synthetic Methods of Organic Chemistry, Vol. 12, (1958), Pub. by S. Karger, N.Y. p. 215, sect. 480 relied on.

*Primary Examiner*—Anton H. Sutto
*Attorney, Agent, or Firm*—Young & Thompson

[57] ABSTRACT

This invention relates to compounds having the formula:

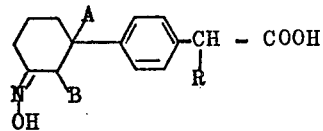

in which R is hydrogen or alkyl containing 1–4 carbon atoms and A and B both represent a hydrogen atom or form together a carbon-carbon bond, and their salts with inorganic or organic bases.

Said compounds have analgesic and anti-inflammatory properties.

2 Claims, No Drawings

PHENYLACETIC ACID DERIVATIVES

The present invention relates to compounds having the formula:

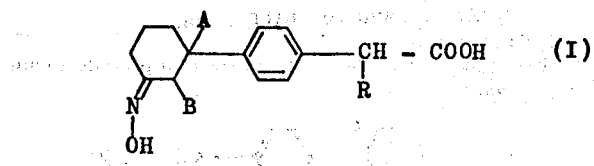

(I)

in which R represents a hydrogen atom or an alkyl group having 1–4 carbon atoms, typically a methyl group, and A and B both represent a hydrogen atom or form together a carbon-carbon bond, and their pharmaceutically acceptable salts with inorganic or organic bases.

The compounds may be prepared in aqueous solution by reaction of hydroxylamine with a salt of the corresponding ketonic compound, typically an alkali metal salt, at room temperature or at slightly more elevated temperature (40°–50°C), followed, if desired, by acidification of the resulting salt to give the acid.

The corresponding ketonic compounds, i.e. the compounds having a formula

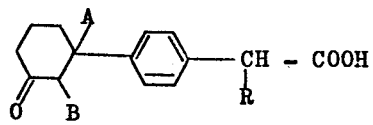

are described in U.S. Pat. Application Ser. No. 285 127.

The following examples illustrate the invention.

EXAMPLE 1

2-[4-(3'-Hydroxyimino-cyclohexen-1'-yl)-phenyl]-propionic acid ( R = CH$_3$; A–b : double bond)

2-[4-(3'-Oxo-cyclohexen-1'-yl)-phenyl]propionic acid (1.27 g;

2- [4-(3'-Oxo-cyclohexen- 5.2 mmoles) is dissolved in N sodium hydroxide (15 ml). Hydroxylamine hydrochloride (0.42 g; 6 mmoles) is added thereto and the resulting solution is allowed to react during 24 hours. The solution is made acidic and the gummy precipitate is then dried and crystallized from water-methanol (1:1), to give 0.83 g of product (Yield: 62%). M.p. = 200°C.

| Analysis: | C$_{15}$H$_{17}$NO$_3$ | C | H | N |
|---|---|---|---|---|
| | Calculated%: | 69,47 | 6.61 | 5.40 |
| | Found% : | 69.5 | 6.9 | 5.35 |

EXAMPLE 2

2-[4-(3'-Hydroxyimino-cyclohexyl)phenyl]propionic acid (R = CH$_3$; A = B = H)

2[4-(3'-Oxo-cyclohexyl)phenyl]propionic acid (4 g; 16.2 mmoles) is dissolved in N sodium hydroxide (55 ml) and treated with hydroxylamine hydrochloride (2.22 g; 32 mmoles) during 24 hours at room temperature. The gummy precipitate formed on acidification is converted to the sodium salt in aqueous solution which is then evaporated to dryness. The residue is dissolved in methanol or ethanol to remove an insoluble. After evaporating off the alcool, the sodium salt is again dissolved in water and converted to the acid which is crystallized from water-methanol (1:1), to give 3 g of product (Yield : 70%), M.p. = 178°C.

| Analysis: | C$_{15}$H$_{19}$NO$_3$ | C | H | N |
|---|---|---|---|---|
| | Calculated %: | 68.94 | 7.33 | 5.36 |
| | Found % : | 68.8 | 7.5 | 5.3 |

EXAMPLE 3

4-(3'-Hydroxyimino-cyclohexen- 1'- yl) -phenylacetic acid (R = H; A-B : double bond)

The procedure described in Example 1 is used. The crude material is recrystallized from dichloroethane and then from acetonitrile. (Yield: 70%). M.p = 180°C

| Analysis: | C$_{14}$H$_{15}$O$_3$N | C | H | N |
|---|---|---|---|---|
| | Calculated %: | 68.55 | 6.16 | 5.71 |
| | Found % : | 68.7 | 6.2 | 5.7 |

EXAMPLE 4

4-(3'-Hydroxyimino-cyclohexyl)phenylacetic acid (R = H, A = B = H)

The procedure described in Example 2 is used. The material is purified by boiling with acetonitrile in which the product is insoluble. (Yield: 64%). M.p. = 190°C.

| Analysis: | C$_{14}$H$_{17}$O$_3$N | C | H | N |
|---|---|---|---|---|
| | Calculated %: | 67.99 | 6.93 | 5.66 |
| | Found % : | 67.8 | 7.0 | 5.7 |

The compounds encompassed by the present invention possess analgesic and anti-inflammatory properties. Said properties were evidenced in animals by means of conventional pharmacological tests.

Analgesic action: Koster test (cf. KOSTER and ANDERSON. Feder. Proceed., 1959, 18, 412)

Antipyretic action, against fever induced by injection of barm, in rats.

Anti-inflammatory action:

carrageenin-induced edema in rats (cf. WINTER, RISLEY and MUSS, Proc. Soc. Exp. Biol. Med., 1962, 111, 544), ultraviolet-induced erythema in guinea-pigs (cf. WINTER, Arch. Int. Pharmaco., 1958, 116, 261), adjuvant-induced polyarthritis in rats, determination of the oral dosage (mg/kg/day) which decreases by at least 50% the manifestations of arthritis within 14 days.

| Compound of Example | 1 | 2 |
|---|---|---|
| Koster test | | |
| ED$_{50}$ (mg/kg p.o.) | 30–50 | 4.5 |
| Antipyretic action | | |
| (mg.kg p.o.) | 30 | 3 |
| Carrageenin-induced edema | | |
| ED$_{40}$ (mg/kg p.o.) | 2.2 | 0.25 |
| UV-induced erythema | | |
| ED$_{50}$ (mg/kg p.o.) | — | 2 |

-continued

| Compound of Example | 1 | | 2 | |
|---|---|---|---|---|
| Polyarthritis | | | | |
| ED₅₀ (p.o.) | — | | 0.9 | |
| LD₅₀ (mg/kg) | I.P. | P.O. | I.P. | P.O. |
| | >100 | >100 | >200 | >200 |

The analgesic and anti-inflammatory properties of the compounds described in this invention are therapeutically useful in human medicine, in the treatment of various pains, particularly of pains of rheumatic origin.

Thus, the present invention relates also to a process for the treatment of pains, comprising administering to human patients a therapeutically effective amount of a compound of the formula (I) or of a pharmaceutically acceptable salt thereof.

The present invention includes also within its scope a therapeutic composition having an analgesic and anti-inflammatory activity, comprising a therapeutically effective amount of a compound of the formula (I) or of a pharmaceutically acceptable salt thereof.

The compounds may be administered as acids, by the oral or rectal route, or as salts with alkali metals or non-toxic organic bases, by the parenteral route, in combination with a carrier suitable for the route of administration chosen.

The daily dosage regimen may vary, depending on the route of administration, from 50 mg to 2 g per 24 hours. Are particularly useful the compositions formulated as tablets or capsules containing 10–200 mg active compound, suppositories containing 10–500 mg active compound or injectable ampoules containing 10–200 mg of a soluble salt.

I claim:
1. A compound selected from the compounds having the formula

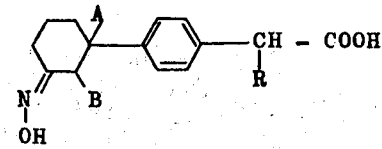

in which R is selected from hydrogen and alkyl having 1–4 carbon atoms and A and B, when taken separately, each represent a hydrogen atom and, when taken together, form a carbon-carbon bond, and their therapeutically acceptable salts with inorganic and organic bases.

2. 2-[4-(3'-Hydroxyimino-cyclohexyl)-phenyl]propionic acid and its therapeutically acceptable salts.

* * * * *